(12) United States Patent
Meyer

(10) Patent No.: US 7,931,606 B2
(45) Date of Patent: Apr. 26, 2011

(54) COMPRESSION APPARATUS

(75) Inventor: Ann Meyer, Shrewsbury, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/299,568

(22) Filed: Dec. 12, 2005

(65) Prior Publication Data

US 2007/0135743 A1 Jun. 14, 2007

(51) Int. Cl.
*A61H 7/00* (2006.01)
(52) U.S. Cl. .............................. 601/152; 602/13; 602/27
(58) Field of Classification Search ................ 602/5, 13, 602/23, 26; 128/882; 607/114; 601/152
See application file for complete search history.

(56) References Cited

U.S. PATENT DOCUMENTS

| | | |
|---|---|---|
| 2,075,229 A | 3/1937 | Rose |
| 2,199,408 A | 5/1940 | Liberte |
| 2,533,504 A | 12/1950 | Poor |
| 2,694,395 A | 11/1954 | Brown |
| 2,708,920 A | 5/1955 | Pasturczak |
| 2,880,721 A | 4/1959 | Corcoran |
| 3,164,152 A | 1/1965 | Nicoll |
| 3,245,405 A | 4/1966 | Gardner |
| 3,454,010 A | 7/1969 | Lilligren et el. |
| 3,506,000 A | 4/1970 | Baker |
| 3,521,623 A | 7/1970 | Nichols et al. |
| 3,561,435 A | 2/1971 | Nicholson |
| 3,598,114 A | 8/1971 | Lewis |
| 3,606,880 A | 9/1971 | Ogle, Jr. |
| 3,701,349 A | 10/1972 | Larson |
| 3,728,875 A | 4/1973 | Hartigan et al. |
| 3,760,795 A | 9/1973 | Adelhed |
| 3,786,805 A | 1/1974 | Tourin |
| 3,824,992 A | 7/1974 | Nicholson et al. |
| 3,826,249 A | 7/1974 | Lee et al. |
| 3,862,629 A | 1/1975 | Rotta |
| 3,866,604 A | 2/1975 | Curless et al. |
| 3,868,952 A | 3/1975 | Hatton |
| 3,877,426 A | 4/1975 | Nirschl |
| 3,888,242 A | 6/1975 | Harris et al. |
| 3,901,221 A | 8/1975 | Nicholson et al. |
| 3,901,225 A | 8/1975 | Sconce |
| 3,920,006 A | 11/1975 | Lapidus |
| 4,013,069 A | 3/1977 | Hasty |
| 4,029,087 A | 6/1977 | Dye et al. |
| 4,030,488 A | 6/1977 | Hasty |
| 4,066,084 A | 1/1978 | Tillander |
| 4,091,804 A | 5/1978 | Hasty |

(Continued)

FOREIGN PATENT DOCUMENTS

EP 1213002 A1 6/2002

(Continued)

OTHER PUBLICATIONS

USPTO Office action issued in U.S. Appl. No. 11/761,212 dated Sep. 4, 2008, 11 pages.

(Continued)

*Primary Examiner* — Michael Brown

(57) ABSTRACT

A compression apparatus is described having a sleeve and an inflatable member disposed within the sleeve, the inflatable member being movable in relation to the sleeve. The compression apparatus includes a hook and loop features attached to the foot sleeve for securing compression apparatus to the feet.

13 Claims, 8 Drawing Sheets

U.S. PATENT DOCUMENTS

| | | | |
|---|---|---|---|
| 4,133,311 A | 1/1979 | Karczewski | |
| 4,153,050 A | 5/1979 | Bishop et al. | |
| 4,156,425 A | 5/1979 | Arkans | |
| 4,168,063 A | 9/1979 | Rowland | |
| 4,198,961 A | 4/1980 | Arkans | |
| 4,202,312 A | 5/1980 | Mori et al. | |
| 4,202,325 A | 5/1980 | Villari et al. | |
| 4,206,751 A | 6/1980 | Schneider | |
| 4,207,875 A | 6/1980 | Arkans | |
| 4,207,876 A | 6/1980 | Annis | |
| 4,253,449 A | 3/1981 | Arkans et al. | |
| 4,270,527 A | 6/1981 | Peters et al. | |
| 4,280,485 A | 7/1981 | Arkans | |
| 4,311,135 A | 1/1982 | Brueckner et al. | |
| 4,320,746 A | 3/1982 | Arkans et al. | |
| 4,338,686 A | 7/1982 | Bell | |
| 4,372,297 A | 2/1983 | Perlin | |
| 4,375,217 A | 3/1983 | Arkans | |
| 4,408,599 A | 10/1983 | Mummert | |
| 4,409,976 A | 10/1983 | Pence | |
| 4,417,587 A | 11/1983 | Ichinomiya et al. | |
| 4,422,834 A | 12/1983 | Drutchas et al. | |
| 4,453,538 A | 6/1984 | Whitney | |
| 4,531,516 A | 7/1985 | Poole et al. | |
| 4,580,816 A | 4/1986 | Campbell et al. | |
| 4,597,384 A | 7/1986 | Whitney | |
| 4,597,385 A | 7/1986 | Watson | |
| 4,614,179 A | 9/1986 | Gardner et al. | |
| 4,614,180 A | 9/1986 | Gardner et al. | |
| 4,632,103 A | 12/1986 | Fabricant et al. | |
| 4,696,289 A | 9/1987 | Gardner et al. | |
| 4,702,232 A | 10/1987 | Gardner et al. | |
| 4,702,234 A | 10/1987 | Huntjens | |
| 4,721,101 A | 1/1988 | Gardner et al. | |
| 4,722,332 A | 2/1988 | Saggers | |
| 4,730,606 A | 3/1988 | Leininger | |
| 4,730,610 A | 3/1988 | Graebe | |
| 4,762,121 A | 8/1988 | Shienfeld | |
| 4,805,601 A | 2/1989 | Eischen, Sr. | |
| 4,827,912 A | 5/1989 | Carrington et al. | |
| RE32,939 E | 6/1989 | Gardner et al. | |
| RE32,940 E | 6/1989 | Gardner et al. | |
| 4,841,956 A | 6/1989 | Gardner et al. | |
| D302,301 S | 7/1989 | Robinette-Lehman | |
| 4,844,058 A | 7/1989 | Vogelbach | |
| 4,883,073 A | 11/1989 | Aziz | |
| 4,920,971 A | 5/1990 | Blessinger | |
| 4,938,208 A | 7/1990 | Dye | |
| 4,945,905 A | 8/1990 | Dye et al. | |
| 4,977,891 A | 12/1990 | Grim | |
| 4,979,953 A | 12/1990 | Spence | |
| 4,993,409 A | 2/1991 | Grim | |
| 5,000,164 A | 3/1991 | Cooper | |
| 5,007,411 A | 4/1991 | Dye | |
| 5,014,681 A | 5/1991 | Heeman et al. | |
| 5,022,387 A | 6/1991 | Hasty | |
| 5,062,414 A | 11/1991 | Grim | |
| 5,069,219 A | 12/1991 | Knoblich | |
| 5,078,128 A | 1/1992 | Grim et al. | |
| 5,094,252 A | 3/1992 | Stumpf | |
| 5,113,877 A | 5/1992 | Johnson, Jr. et al. | |
| 5,193,549 A | 3/1993 | Bellin et al. | |
| 5,218,954 A | 6/1993 | van Bemmelen | |
| 5,235,703 A | 8/1993 | Maynard | |
| D341,424 S | 11/1993 | Lurie | |
| 5,277,697 A | 1/1994 | France et al. | |
| 5,288,286 A | 2/1994 | Davis et al. | |
| 5,310,400 A | 5/1994 | Rogers et al. | |
| 5,334,135 A | 8/1994 | Grim et al. | |
| 5,354,260 A | 10/1994 | Cook | |
| 5,372,575 A | 12/1994 | Sebastian | |
| RE34,883 E | 3/1995 | Grim | |
| 5,396,896 A | 3/1995 | Tumey et al. | |
| 5,399,152 A | 3/1995 | Habermeyer et al. | |
| 5,400,529 A | 3/1995 | Bell et al. | |
| 5,407,418 A | 4/1995 | Szpur | |
| 5,407,421 A * | 4/1995 | Goldsmith | 602/5 |
| D358,216 S | 5/1995 | Dye | |
| 5,413,582 A | 5/1995 | Eaton | |
| 5,415,624 A | 5/1995 | Williams | |
| 5,425,742 A | 6/1995 | Joy | |
| 5,450,858 A | 9/1995 | Zablotsky et al. | |
| 5,453,082 A | 9/1995 | Lamont | |
| 5,458,562 A | 10/1995 | Cooper | |
| 5,464,385 A | 11/1995 | Grim | |
| 5,484,392 A | 1/1996 | Sydor et al. | |
| D376,013 S | 11/1996 | Sandman et al. | |
| 5,575,762 A | 11/1996 | Peeler et al. | |
| 5,577,998 A | 11/1996 | Johnson, Jr. et al. | |
| 5,584,798 A | 12/1996 | Fox | |
| 5,588,955 A | 12/1996 | Johnson, Jr. et al. | |
| 5,591,200 A | 1/1997 | Cone et al. | |
| 5,626,556 A | 5/1997 | Tobler et al. | |
| 5,634,889 A | 6/1997 | Gardner et al. | |
| 5,649,954 A | 7/1997 | McEwen | |
| 5,653,244 A | 8/1997 | Shaw | |
| 5,660,182 A | 8/1997 | Kuroshaki et al. | |
| 5,669,390 A | 9/1997 | McCormick et al. | |
| 5,669,872 A | 9/1997 | Fox | |
| 5,674,262 A | 10/1997 | Tumey | |
| 5,678,558 A | 10/1997 | Johnson | |
| 5,688,225 A | 11/1997 | Walker | |
| 5,690,672 A | 11/1997 | Cohen | |
| 5,711,757 A | 1/1998 | Bryant | |
| 5,733,249 A | 3/1998 | Katzin et al. | |
| 5,746,213 A * | 5/1998 | Marks | 600/499 |
| 5,769,801 A | 6/1998 | Tumey et al. | |
| 5,795,312 A | 8/1998 | Dye | |
| 5,797,851 A | 8/1998 | Byrd | |
| D397,797 S | 9/1998 | Chiang | |
| 5,806,208 A | 9/1998 | French | |
| 5,823,981 A | 10/1998 | Grim et al. | |
| 5,830,164 A * | 11/1998 | Cone et al. | 601/152 |
| 5,833,639 A * | 11/1998 | Nunes et al. | 602/23 |
| 5,840,049 A | 11/1998 | Tumey et al. | |
| 5,843,007 A | 12/1998 | McEwen et al. | |
| D405,180 S | 2/1999 | Reina | |
| 5,864,880 A | 2/1999 | Adam | |
| 5,868,690 A | 2/1999 | Eischen, Sr. | |
| 5,876,359 A | 3/1999 | Bock et al. | |
| 5,891,065 A | 4/1999 | Cariapa et al. | |
| D411,301 S | 6/1999 | Hampson et al. | |
| 5,931,797 A | 8/1999 | Tumey et al. | |
| 5,951,502 A | 9/1999 | Peeler et al. | |
| 5,954,676 A | 9/1999 | Kramer, III | |
| 5,971,947 A | 10/1999 | McNally et al. | |
| 5,987,779 A | 11/1999 | Litchfield et al. | |
| 5,988,704 A | 11/1999 | Ryhman | |
| 5,989,204 A | 11/1999 | Lina | |
| 5,991,654 A | 11/1999 | Tumey et al. | |
| 5,997,495 A | 12/1999 | Cook et al. | |
| 6,001,122 A | 12/1999 | Lyles | |
| 6,010,471 A | 1/2000 | Ben-Noon | |
| 6,014,823 A | 1/2000 | Lakic | |
| 6,024,714 A | 2/2000 | Katzin | |
| 6,036,718 A | 3/2000 | Ledford et al. | |
| 6,066,107 A | 5/2000 | Habermeyer | |
| 6,083,185 A | 7/2000 | Lamont | |
| 6,228,044 B1 | 5/2001 | Jensen et al. | |
| 6,245,023 B1 | 6/2001 | Clemmons | |
| 6,273,866 B2 | 8/2001 | Thomas et al. | |
| 6,290,662 B1 | 9/2001 | Morris et al. | |
| 6,293,918 B1 | 9/2001 | Wang | |
| 6,306,112 B2 | 10/2001 | Bird | |
| 6,319,215 B1 | 11/2001 | Manor et al. | |
| 6,361,496 B1 | 3/2002 | Zikorus et al. | |
| 6,361,548 B1 | 3/2002 | McEwen | |
| 6,406,450 B1 | 6/2002 | Kowalczyk et al. | |
| 6,416,534 B1 | 7/2002 | Montagnino et al. | |
| 6,423,017 B2 | 7/2002 | Brotz | |
| 6,436,064 B1 | 8/2002 | Kloecker | |
| 6,440,093 B1 | 8/2002 | McEwen et al. | |
| 6,447,460 B1 | 9/2002 | Zheng et al. | |
| 6,447,467 B1 | 9/2002 | Barak | |
| 6,460,197 B2 | 10/2002 | Huang | |
| 6,463,934 B1 | 10/2002 | Johnson, Jr. et al. | |
| 6,468,237 B1 | 10/2002 | Lina | |

| | | |
|---|---|---|
| 6,478,745 B2 | 11/2002 | Nakagawa et al. |
| 6,478,757 B1 | 11/2002 | Barak |
| 6,488,643 B1 * | 12/2002 | Tumey et al. .................. 602/13 |
| 6,493,568 B1 | 12/2002 | Bell et al. |
| 6,494,852 B1 | 12/2002 | Barak et al. |
| 6,506,206 B1 | 1/2003 | Guzman et al. |
| 6,525,238 B2 | 2/2003 | Corrales |
| 6,528,697 B1 | 3/2003 | Knutson et al. |
| 6,537,298 B2 | 3/2003 | Dedo |
| 6,544,202 B2 | 4/2003 | McEwen et al. |
| 6,551,249 B2 | 4/2003 | Ashida et al. |
| 6,551,264 B1 | 4/2003 | Cawley et al. |
| 6,557,704 B1 | 5/2003 | Randolph |
| 6,582,383 B2 | 6/2003 | Horning |
| 6,585,669 B2 | 7/2003 | Manor et al. |
| 6,589,194 B1 | 7/2003 | Calderon et al. |
| 6,589,534 B1 | 7/2003 | Shaul et al. |
| 6,592,534 B1 | 7/2003 | Rutt et al. |
| 6,629,941 B1 | 10/2003 | Ishibashi et al. |
| 6,632,188 B2 | 10/2003 | Thomas et al. |
| D482,792 S | 11/2003 | McCormick et al. |
| 6,672,311 B2 | 1/2004 | Rindfleish |
| 6,681,772 B2 | 1/2004 | Atwater et al. |
| 6,682,497 B2 | 1/2004 | Jensen et al. |
| 6,766,599 B2 | 7/2004 | Baek |
| 6,785,985 B2 | 9/2004 | Marvin et al. |
| 6,869,409 B2 | 3/2005 | Rothman et al. |
| 6,893,409 B1 | 5/2005 | Lina |
| 6,916,298 B2 | 7/2005 | VanBrunt et al. |
| 6,918,393 B2 | 7/2005 | Rugfelt et al. |
| 6,921,373 B1 | 7/2005 | Bernstein |
| 6,945,944 B2 | 9/2005 | Kuiper et al. |
| D513,324 S | 12/2005 | Cook et al. |
| 6,988,329 B2 | 1/2006 | Marvin et al. |
| 6,988,992 B2 | 1/2006 | Just et al. |
| D517,695 S | 3/2006 | Gillis et al. |
| 7,008,390 B2 | 3/2006 | Miotto et al. |
| 7,010,823 B2 | 3/2006 | Baek |
| 7,047,670 B2 | 5/2006 | Marvin et al. |
| 7,070,567 B2 | 7/2006 | Mizukoshi et al. |
| 7,104,967 B2 | 9/2006 | Rothman et al. |
| 7,135,007 B2 | 11/2006 | Scott et al. |
| 7,150,720 B2 | 12/2006 | Adkins et al. |
| 7,153,270 B2 | 12/2006 | Sano et al. |
| 7,166,077 B2 | 1/2007 | Millay et al. |
| 7,282,038 B2 | 10/2007 | Gillis et al. |
| D569,985 S | 5/2008 | Ganapathy et al. |
| 7,374,550 B2 | 5/2008 | Hansen et al. |
| 7,384,584 B2 | 6/2008 | Jerome et al. |
| 2001/0018564 A1 | 8/2001 | Manor et al. |
| 2002/0022791 A1 | 2/2002 | Morris et al. |
| 2002/0042583 A1 | 4/2002 | Barak et al. |
| 2002/0069731 A1 * | 6/2002 | Soucy ............................ 82/163 |
| 2002/0099297 A1 | 7/2002 | Nakagawa et al. |
| 2002/0133106 A1 | 9/2002 | Peled |
| 2002/0188315 A1 | 12/2002 | Guzman et al. |
| 2003/0036771 A1 | 2/2003 | McEwen et al. |
| 2003/0125649 A1 | 7/2003 | McIntosh et al. |
| 2003/0139696 A1 | 7/2003 | Boukanov et al. |
| 2003/0139766 A1 | 7/2003 | McEwen et al. |
| 2003/0187378 A1 | 10/2003 | Gaylord et al. |
| 2004/0039317 A1 | 2/2004 | Souney et al. |
| 2004/0064077 A1 | 4/2004 | Dillon |
| 2004/0068290 A1 | 4/2004 | Bates et al. |
| 2004/0171971 A1 | 9/2004 | Ravikumar et al. |
| 2004/0181156 A1 | 9/2004 | Kingsford et al. |
| 2004/0236258 A1 | 11/2004 | Burns et al. |
| 2005/0027218 A1 | 2/2005 | Filtvedt et al. |
| 2005/0121041 A1 | 6/2005 | Barnitz |
| 2005/0131321 A1 * | 6/2005 | Ravikumar .................. 602/13 |
| 2005/0143682 A1 | 6/2005 | Cook et al. |
| 2005/0145256 A1 | 7/2005 | Howard et al. |
| 2005/0171461 A1 | 8/2005 | Pick |
| 2005/0187500 A1 * | 8/2005 | Perry et al. .................. 601/152 |
| 2005/0187501 A1 | 8/2005 | Ravikumar |
| 2005/0203452 A1 | 9/2005 | Weston et al. |
| 2005/0211580 A1 | 9/2005 | Kaszubski et al. |
| 2005/0215935 A1 | 9/2005 | Ritter |
| 2005/0261615 A1 | 11/2005 | Weston |
| 2006/0004310 A1 | 1/2006 | Parizot |
| 2006/0004311 A1 | 1/2006 | Hargrave et al. |
| 2006/0135894 A1 | 6/2006 | Linnane et al. |
| 2006/0161081 A1 | 7/2006 | Barak et al. |
| 2006/0178606 A1 | 8/2006 | Logue et al. |
| 2006/0189905 A1 | 8/2006 | Eischen, Sr. |
| 2006/0189907 A1 | 8/2006 | Pick et al. |
| 2007/0010765 A1 | 1/2007 | Rothman et al. |
| 2007/0010770 A1 | 1/2007 | Gildersleeve |
| 2007/0049852 A1 | 3/2007 | Linnane et al. |
| 2007/0135743 A1 | 6/2007 | Meyer |
| 2007/0135836 A1 | 6/2007 | McEwen et al. |
| 2007/0161933 A1 | 7/2007 | Ravikumar |
| 2007/0282233 A1 | 12/2007 | Meyer et al. |

FOREIGN PATENT DOCUMENTS

| | | | |
|---|---|---|---|
| FR | 2813770 A1 * | 3/2002 | |
| WO | WO2005/055913 | * | 6/1995 |
| WO | WO 95/18594 A | 7/1995 | |
| WO | WO 2005/055913 A | 6/2005 | |

OTHER PUBLICATIONS

USPTO Office Action issued in U.S. Appl. No. 12/059,828 dated Oct. 29, 2008, 23 pages.

Tyco Healthcare Kendall, Prevention Gets Personal, Mar. 2001, pp. 1, 2, 4.

Tyco Healthcare Kendall, SCD Response Brochure, Mar. 2000, pp. 1-2.

Tyco Healthcare Kendall, SCD Soft Sleeve Brochure, Apr. 2001, pp. 1-2.

The Kendall Company, Vascular Therapy Products Catalog, Jan. 1996, pp. 8-5-8-7.

Final Rejection dated Jun. 10, 2009 from related U.S. Appl. No. 11/761,212, 13 pgs.

Final Rejection dated Jun. 25, 2009 from related U.S. Appl. No. 12/059,828, 24 pgs.

* cited by examiner

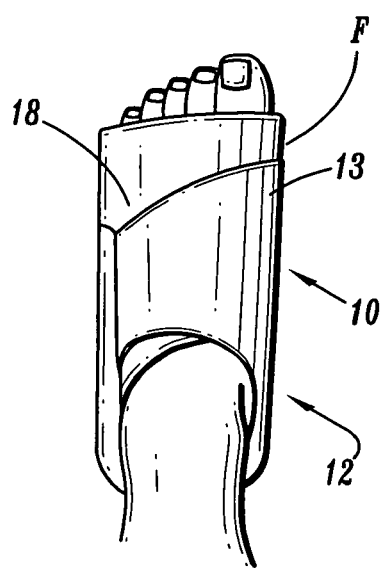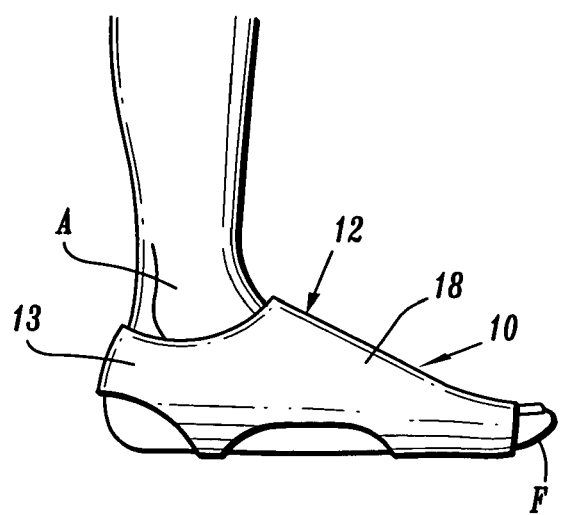
FIG. 8     FIG. 9

COMPRESSION APPARATUS

BACKGROUND

1. Technical Field

The present disclosure relates generally to compression apparatus. In particular, the present disclosure relates to a compression apparatus configured for applying compressive forces to a portion of a patient's anatomy.

2. Description of the Related Art

Compression devices for applying compressive forces to a selected area of a person's anatomy are generally employed to improve blood flow in the selected area. Compression devices that provide intermittent pulses of a compressed fluid (i.e. air) to inflate at least one inflatable chamber in a sleeve are particularly useful. This cyclic application of pressure provides a non-invasive method of prophylaxis to reduce the incidence of deep vein thrombosis (DVT), and the like. These compression devices find particular use during surgery on patients with high-risk conditions such as obesity, advanced age, malignancy, or prior thromboembolism. Patients who develop this condition often have swelling (edema) and tissue breakdown (venous stasis ulcer) in the lower leg. When a DVT occurs, the valves that are located within the veins of the leg can be damaged, which in turn can cause stasis and high pressure in the veins of the lower leg.

Generally, these compression devices are fluidly coupled to a source of pressurized fluid by one or more air tubes. Additionally, each compression device includes a flexible shell having one or more inflatable members disposed therein. The compression device is placed around the patient's foot or other selected portion whereupon a pressurized fluid is delivered into the inflatable member creating pressure at the part or parts of the body in contact with the inflatable member.

Compression sleeves adapted for use with a patient's foot may be combined with one or more additional compression sleeves that are disposed on portions of a patient's leg for improving the treatment regimen. In general, each of the additional compression sleeves includes a plurality of separate inflatable chambers that are progressively arranged along a longitudinal axis of the sleeve from a lower portion to an upper portion of the limb. A pressure source, e.g. a controller, is provided for intermittently forming a pressure pulse within these inflatable chambers from a source of pressurized fluid during periodic compression cycles. The compression sleeves provide a pressure gradient along the patient's limbs during these compression cycles which progressively decreases from the lower portion to the upper portion of the limb (e.g. from the ankle to the thigh).

Compression sleeves that are adapted for use with a patient's foot generally include a heel strap with a tab portion that is adapted to fit around a portion of the patient's heel. This arrangement allows the compression sleeve to be releasably attached to the patient's foot.

Examples of compression sleeves are disclosed in U.S. Pat. Nos. 4,013,069 and 4,030,488 to Hasty, U.S. Pat. Nos. 4,029,087 and 5,795,312 to Dye, and U.S. Pat. No. 5,626,556 to Tobler et al., all of which are currently owned by Tyco Healthcare Group LP and are incorporated by reference herein in their entirety. Other examples of compression sleeves are disclosed in U.S. Pat. No. 4,696,289 to Gardner et al. and U.S. Pat. No. 5,989,204 to Lina. An example of compression treatment method is disclosed in U.S. Pat. No. 6,231,532 to Watson et al., which is currently owned by Tyco Healthcare Group LP, the contents of which are hereby incorporated by reference herein in their entirety.

Some prior art devices are bulky and may irritate portions of the limb undergoing treatment which may increase patient discomfort and may increase the possibility that the patient may not complete the treatment regimen.

SUMMARY

The present disclosure is directed towards a compression apparatus for applying compressive forces to a selected portion of a patient's anatomy. The compression apparatus includes a sleeve and at least one inflatable member disposed within the sleeve, the at least one inflatable member being freely movable or repositionable in relation to the foot sleeve. The compression apparatus further includes hook and loop features attached thereto for securing the compression apparatus to the selected portion of the patient's anatomy.

In one embodiment, the compression apparatus includes a foot sleeve for applying compressive forces to a patient's foot. The foot sleeve includes an inflatable member disposed therewithin, the inflatable member being freely movable in relation to the foot sleeve. The foot sleeve includes a contact layer and an outer layer. The contact layer and the outer layer are fixedly joined by radio frequency (RF) welding, or by other suitable methods, along their corresponding perimeters thereby defining a space therebetween. The outer surface of the contact layer contacts the bottom portion of the foot and it may be fabricated from a chemically treated material having a mesh-like fabric with wicking ability. The outer layer may be fabricated from a laminated material having a soft material for cushioning effect against the skin. In addition, the outer layer provides the attachment surface for the hook and loop features.

The inflatable member is configured for receiving and retaining a pressurized fluid from a pressurized fluid source for exerting compressive pressure on a portion of the patient's foot during successive pressure applying cycles. In addition, the inflatable member is dimensioned for being disposed within the space defined by the contact and outer layers of the foot sleeve. The inflatable member includes an upper layer having a two part laminated material for sliding against the foot contact layer and a lower layer configured for anchoring to the outside layer of the foot sleeve. Alternatively, the inflatable member is configured and adapted to be freely movable with respect to the contact and outer layers of the foot sleeve.

In a second embodiment, the compression apparatus includes a compression sleeve for applying compressive pressure against a portion of a patient's limbs, such as, for example, the legs. The compression sleeve includes a sleeve having a pair of opposed sheets attached to one another along their respective perimeters and defining at least one chamber. The at least one chamber is configured for receiving at least one inflatable member wherein the at least one inflatable member is freely movable or repositionable in relation to the sleeve. The inflatable member is configured for receiving and retaining a pressurized fluid from a pressurized fluid source for exerting compressive pressure on a portion of a patient's leg during successive pressure applying cycles.

Other features will become apparent from the following detailed description, taken in conjunction with the accompanying drawings, which illustrate, by way of example, the presently disclosed compression apparatus.

BRIEF DESCRIPTION OF THE DRAWINGS

The features of the presently disclosed compression apparatus will become more readily apparent by referring to the following detailed description of embodiments, which are described hereinbelow with reference to the drawings, wherein:

FIG. 8 is a top plan view of the compression apparatus of FIG. 1 disposed about a foot of a patient;

FIG. 9 is a side plan view of the compression apparatus of FIG. 1 disposed about a foot of a patient;

DETAILED DESCRIPTION

Figure 1:
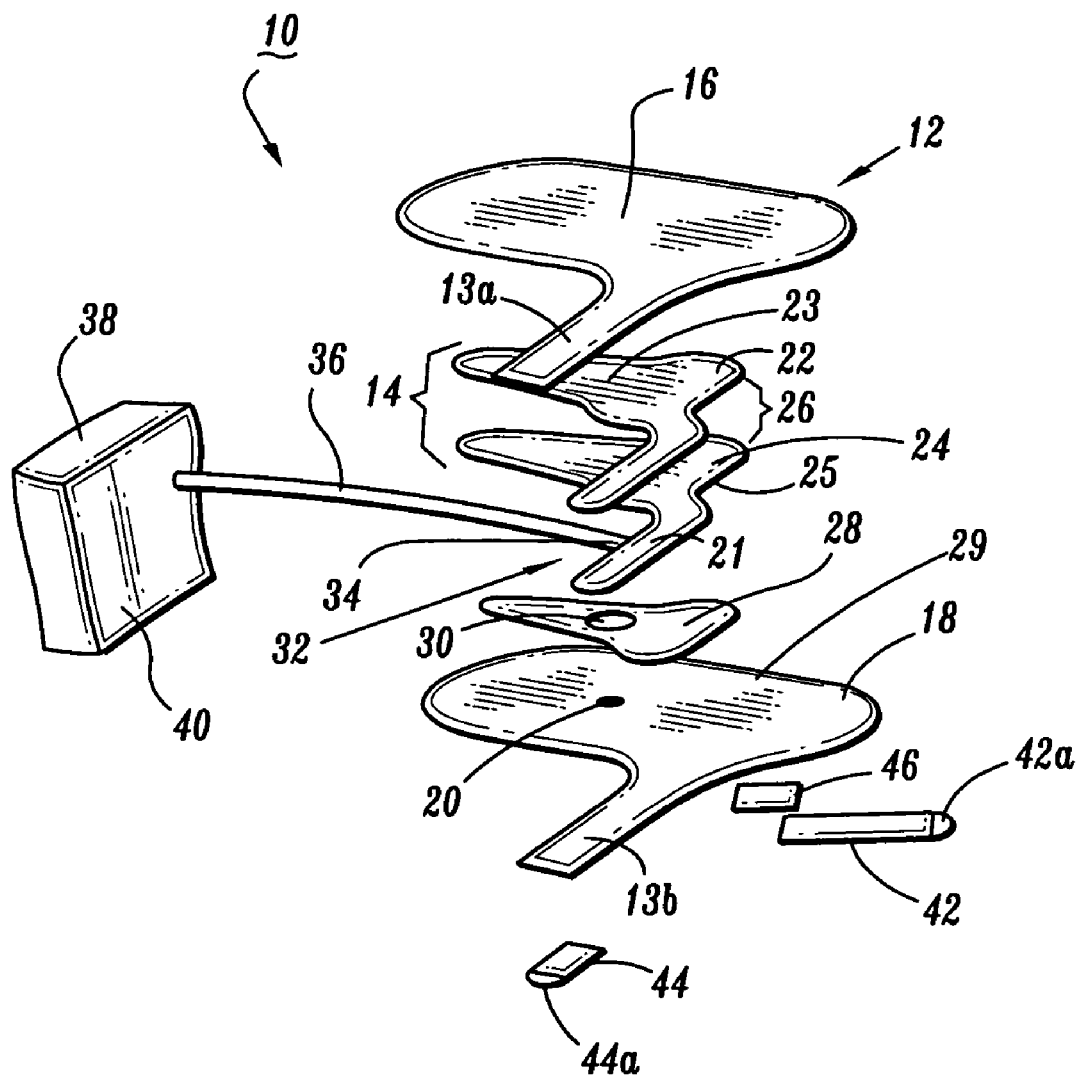
FIG. 1 is a perspective view, with parts separated, of a first embodiment of the compression apparatus in accordance with the present disclosure.
Figure 2:
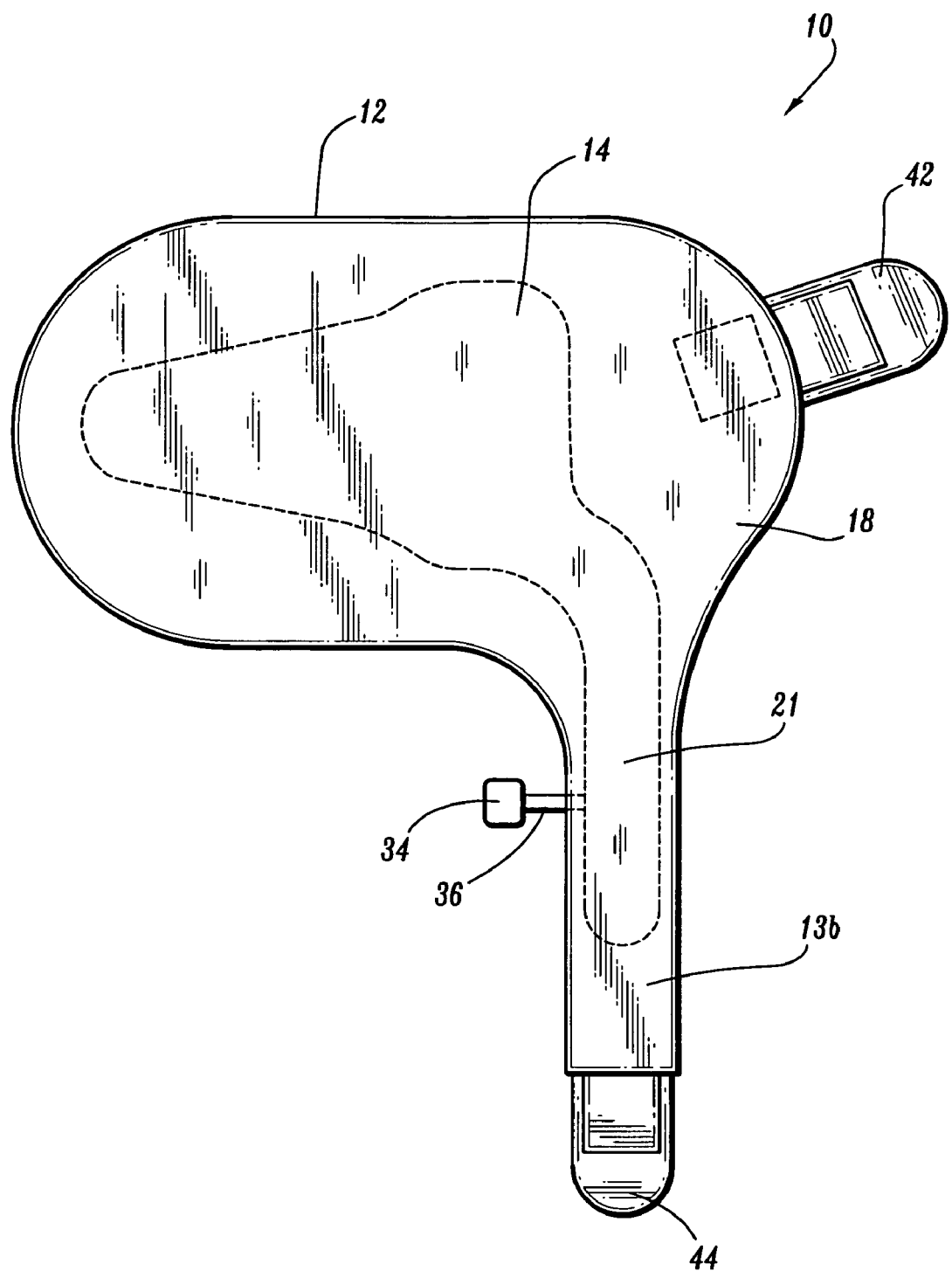
FIGS. 2-3 are top and bottom plan views respectively, of the compression apparatus illustrated in FIG. 1.

With reference to the drawing figures, in which like references numerals identify identical or corresponding elements, various embodiments of the presently disclosed compression apparatus will now be described in detail.

With initial reference to FIGS. 1-4, a first embodiment of a compression apparatus in accordance with the present disclosure is illustrated and is designated generally as compression apparatus 10. Compression apparatus 10 is adapted for use in a system for applying compressive pressure to a portion of a body, such as, for example, a foot of a person. Compression apparatus 10 generally includes a foot sleeve 12 configured for disposal about a foot and an inflatable member 14 disposed within foot sleeve 12 and being freely movable or repositionable in relation to foot sleeve 12. Moreover, foot sleeve 12 is configured and dimensioned for disposing about the right or left foot of the subject.

Figures 3, 4:
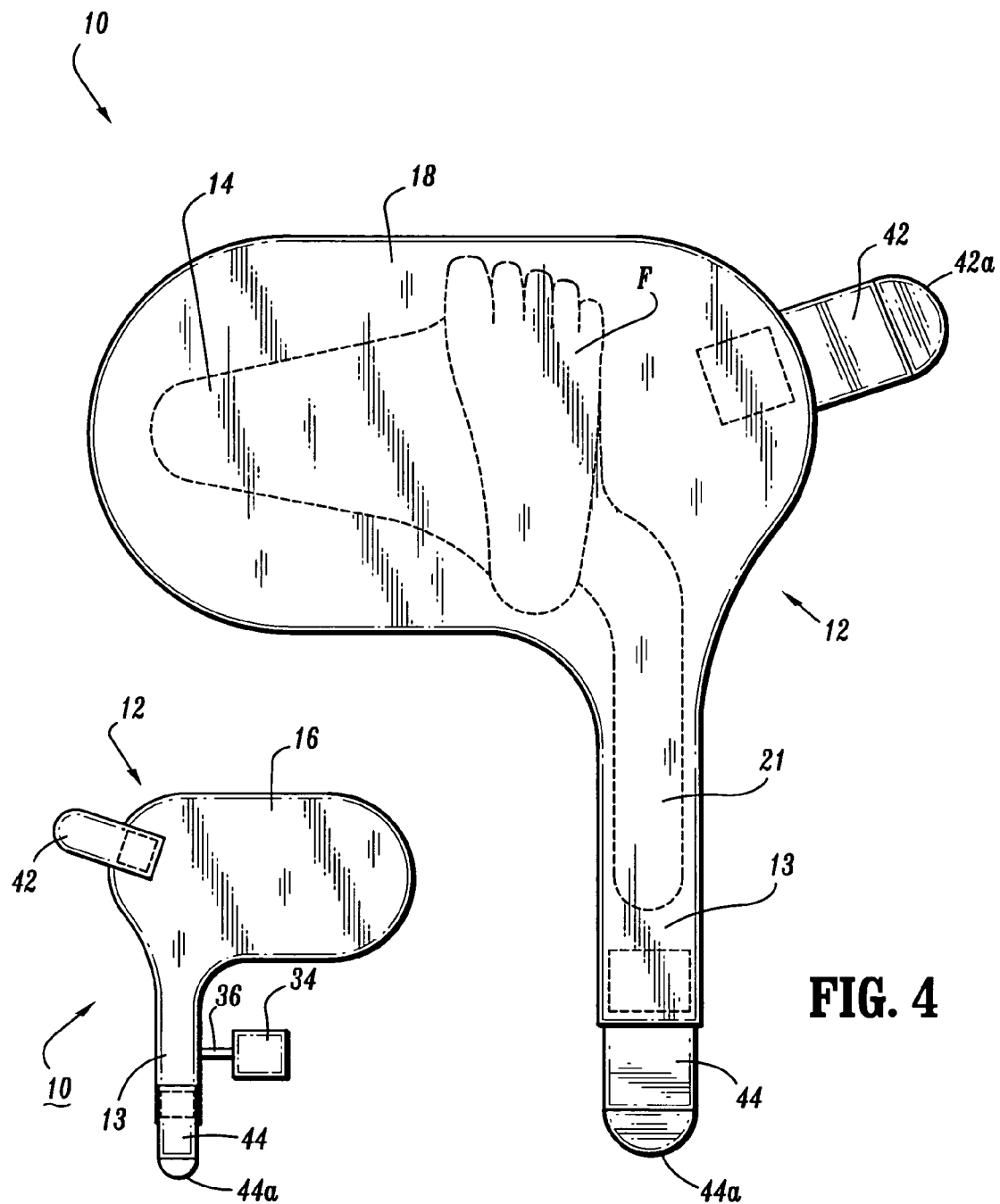
FIG. 4 is a bottom plan view of the compression apparatus of FIG. 1, illustrating a foot of a patient disposed thereon, in accordance with the present disclosure.

Foot sleeve 12 includes a contact layer 16 and an outer layer 18 fixedly joined at seams adjacent corresponding perimeters thereof and defining a space for receiving inflatable member 14 therein. Contact layer 16 and outer layer 18 may be joined by radio frequency (RF) welding, sewing, adhesives, etc. Contact layer 16 and outer layer 18 include strap portions 13a and 13b respectively. Strap portions 13a, 13b have a longitudinally projecting configuration for wrapping about a portion of the foot adjacent to the ankle. Contact layer 16 is adapted for contacting the bottom portion of the foot and providing a fabric on fabric slide with inflatable member 14, in accordance with the present disclosure. Strap portions 13a, 13b (FIG. 1) are joined together to form a strap portion 13 (FIG. 3). Strap portions 13a, 13b can be sewn, RF welded, or sonic welded. Contact layer 16 is fabricated from a chemically treated material, with wicking ability, for wicking away moisture from the skin. In one embodiment, contact layer 16 includes a mesh-like fabric capable of wicking moisture away from the patient's skin. Furthermore, the contact layer 16 can be faced with a soft material toward the treatment surface of the patient. The material can be a thin layer of open celled porous foam, napped cloth, or a layer of vapor permeable cloth permeable.

Outer layer 18 includes an opening 20 for permitting a pressurized fluid inlet passage therethrough, in a manner described herein below. Outer layer 18 is configured for providing the attachment surface for a hook and loop feature of compression apparatus 10, as will be described in detail hereinbelow. Moreover, outer layer 18 provides a soft material for cushioning effect against the top portion of the feet and may be fabricated from similar materials as contact layer 16 and in similar dimensions therewith for corresponding geometry. Alternatively, outer layer 18 may be fabricated from a laminated material, such as, for example, sontara fabric, open cell urethane foam, or loop fabric.

With particular reference to FIG. 1, inflatable member 14 is disposed within the space defined by contact layer 16 and outer layer 18 and is configured for moving independently relative to foot sleeve 12. Inflatable member 14 is configured for positioning against the bottom portion of the feet and the ankle portion. Inflatable member 14 is adapted for receiving and retaining a pressurized fluid (e.g. air) for exerting compressive pressure to the foot during successive pressure applying cycles. An inflatable strap portion 21 is in fluid communication with inflatable member 14 and extends substantially within the space defined by strap portions 13a and 13b of contact layer 16 and outer layer 18 respectively. Inflatable member 14 includes upper and lower inflatable layers 22, 24 overlaid to form an inflatable portion. Upper and lower layers 22, 24 are fixedly joined via sealing lines 26 along their perimeters to define the inflatable portion. Sealing lines 26 may be formed by radio frequency (RF) welding. Alternatively, sealing lines 26 may be sewn, formed by adhesive, heat sealing, etc.

A first surface 23 of upper inflatable layer 22 is positioned just below contact layer 16 for providing the largest compression effect on the foot. Surface 23 of upper inflatable layer 22 releasably engages contact layer 16 for facilitating application of pressure for vascular therapy to the foot. Upper inflatable layer 22 includes material for wicking away moisture from the bottom of the feet. In one embodiment, upper inflatable layer 22 includes a two-part laminated material that is formed from a chemically treated wicking fabric or sontara material combined with a suede finish thereby allowing layer 22 to move with respect to contact layer 16.

Lower inflatable layer 24 includes a single material such as a polyvinyl chloride (PVC) having a suede finish. It is envisioned that the material used to fabricate lower inflatable layer 24 may include at least two different thicknesses for providing directional inflation of inflatable member 14. Thus, inflation of inflatable member 14 yields different shapes as determined by the thickness of inflatable member 14.

An adhesive layer 28 is provided for anchoring an outer surface 25 of lower inflatable layer 24 to an interior surface 29 of outside layer 18 of foot sleeve 12. Therefore, inflatable member 14 is freely movable or repositionable with respect to contact layer 16. An opening 30 positioned on adhesive layer 28 is aligned with opening 20 of outer layer 18 of foot sleeve 12 for permitting the pressurized fluid inlet therethrough. Adhesive layer 28 may be fabricated from a double sided adhesive material. In an alternative embodiment, inflatable member 14 may be freely movable or repositionable with respect to both contact layer 16 and outside layer 18, eliminating adhesive layer 28. Additionally, adhesive layer 28 may be positioned between contact layer 16 and surface 23. This arrangement allows outer layer 18 to move freely with respect to outer surface 25.

With continued reference to FIG. 1, inflatable member 14 further includes an inflation assembly 32 for supplying or removing a pressurized fluid (i.e. air) to inflatable member 14. Inflation assembly 32 includes a valve connector (not shown) having a port 34 (FIGS. 2 and 3) coupled to lower inflatable layer 24 and a lumen 36. Lumen 36 fluidly connects the inflatable member 14 to a pressurized fluid source 38. It is noted that the valve connector (not shown) protrudes from openings 30 and 20 for providing access to inflatable member 14. An example of a suitable valve connector is disclosed in U.S. Pat. No. 5,478,119 to Dye, currently owned by and assigned to Tyco Healthcare Group LP, the entire contents of which is hereby incorporated by reference herein. Pressurized fluid source 38 is disposed within a controller 40 that is adapted for delivering fluid under pressure for performing vascular therapy. An example of a suitable controller 40 is disclosed in U.S. Pat. No. 5,876,359 to Bock et al., currently owned by and assigned to Tyco Healthcare Group LP, the entire contents of which is hereby incorporated by reference herein. It is contemplated that controller 40 may include the necessary electronics and/or computer software to provide vascular therapy, in accordance with the present disclosure, and may be stationary or portable. Alternatively, controller 40 does not include a source of pressurized fluid, but fluidly couples pressurized fluid source 38 to foot sleeve 12, wherein controller 40 controls the delivery of pressurized fluid to foot sleeve 12 for performing vascular therapy.

Referring now to FIGS. 1 and 4, a plurality of hook fasteners 42, 44 are provided for attaching compression apparatus 10 to a foot F, and are positioned on outer layer 18 of foot sleeve 12. Hook 44 is mounted to strap portion 13b of outer layer 18 of foot sleeve 12 while hook 42 is mounted on a surface of outer layer 18. In use, when strap portion 13 is wrapped about foot F, hook element 44 engages outer layer 18 to facilitate mounting of foot sleeve 12 to foot F. In addition, inflatable strap portion 21 of inflatable member 14 is disposed about foot F for compression therapy. An identification tab 46 may also be included for providing information such as the model number and manufacturer name. Hook fasteners 42, 44 have tabs 42a, 44a without fastening material thereon. This provides convenient gripping locations on hook fasteners 42, 44, thereby allowing the practitioner to easily remove hooks 42, 44 from the surface of outer layer 18.

Figure 5:
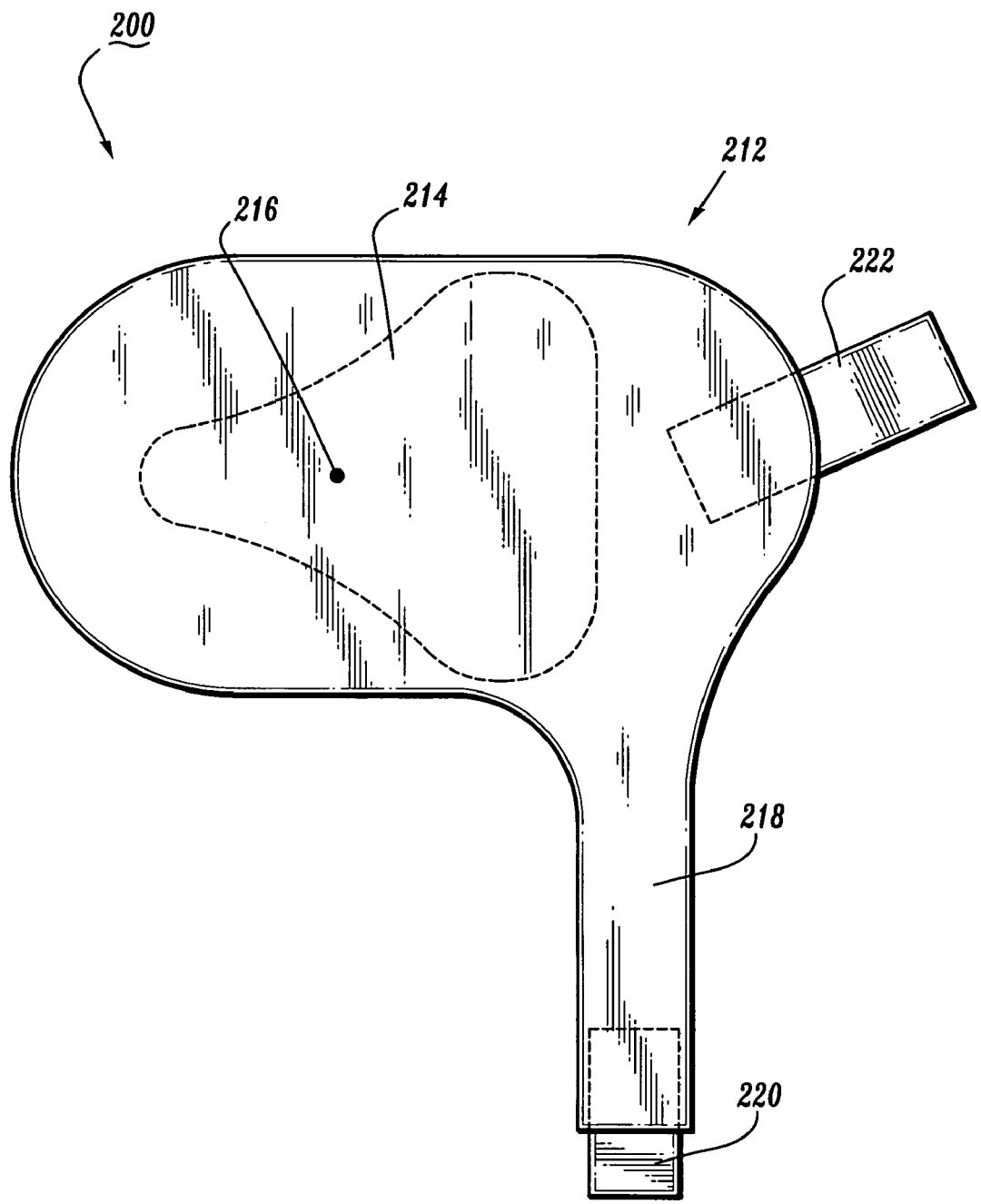
FIG. 5 is a bottom plan view of an alternative embodiment of a compression apparatus, in accordance with the present disclosure.
Figure 6:
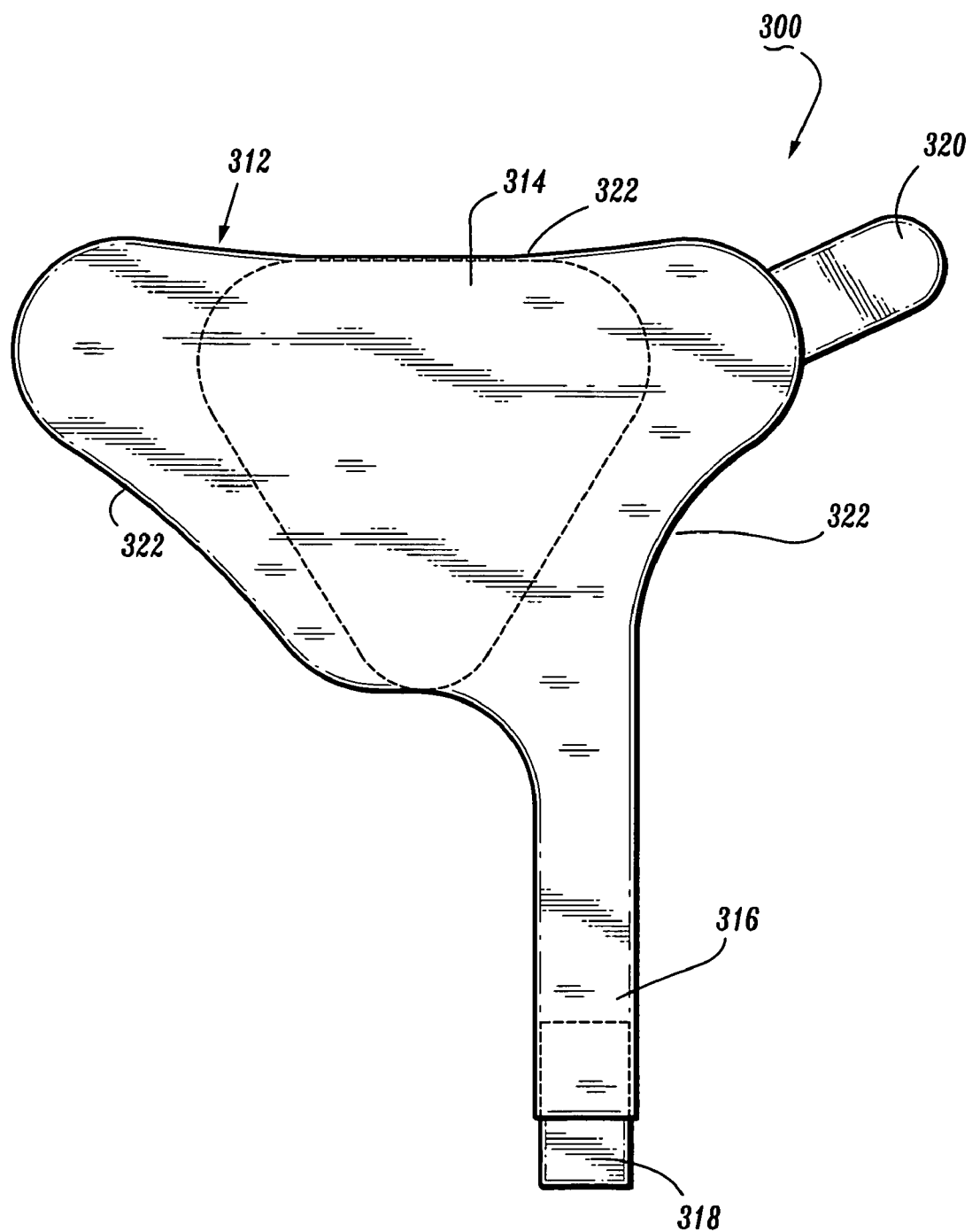
FIGS. 6-7 are top plan views of further alternative embodiments of a compression apparatus, in accordance with the present disclosure.
Figure 7:
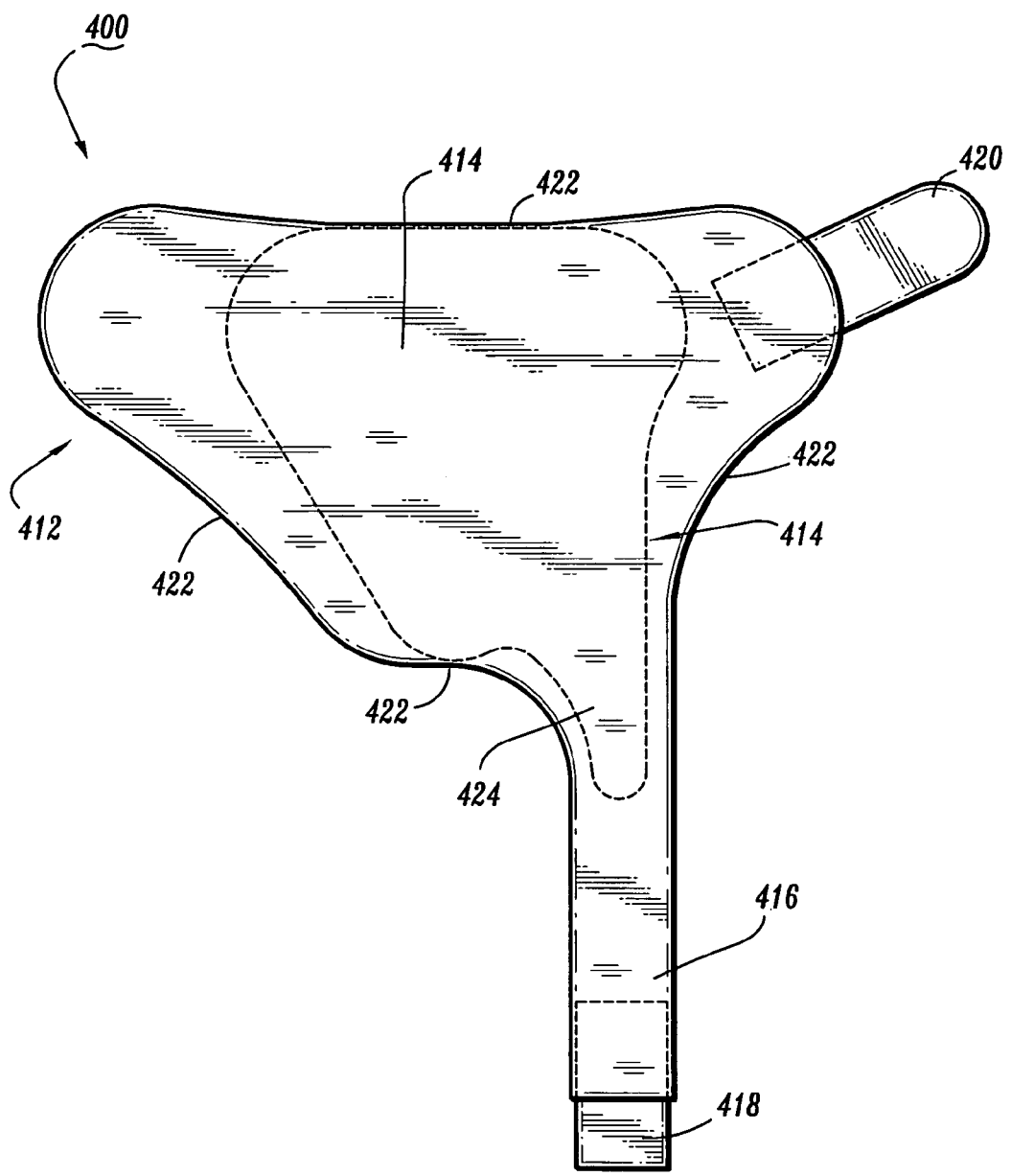

With reference to FIGS. 5-7, alternative embodiments of the compression apparatus 10 of FIGS. 1-4 are illustrated. These embodiments are similar to the embodiment illustrated in FIGS. 1-4 and will only be discussed in detail to the extent necessary to identify differences in construction and operation.

With particular reference to FIG. 5, compression apparatus 200 includes foot sleeve 212 and inflatable member 214, shown in phantom. Foot sleeve 212 includes first and second layers defining a space therebetween for receiving inflatable member 214 therein, which are similar to upper and lower inflatable layers 22, 24 (FIG. 1). Inflatable member 214 is configured for independent movement relative to at least one of first or second layers. Inflatable member 214 includes a valve connector 216 for connecting inflatable member 214 to a pressurized fluid source. Valve connector 216 protrudes through an opening positioned on the outer sleeve portion of foot sleeve 212, in a manner described hereinabove with respect to compression apparatus 10. Foot sleeve 212 includes strap portion 218 extending longitudinally therethrough. A hook element 220 attached to a distal end of strap portion 218, and a hook element 222 is mounted to a portion of the foot sleeve 212. Inflatable member 214 is configured and dimensioned for substantial fit within foot sleeve 212, wherein foot sleeve 212 is configured to be wrapped around the bottom portion of the foot.

With reference to FIG. 6, compression apparatus 300 includes foot sleeve 312 and inflatable member 314, shown in phantom. Foot sleeve 312 includes first and second layers defining a space therebetween that receives inflatable member 314 therein, which are similar to upper and lower inflatable layers 22, 24 (FIG. 1). Inflatable member 314 is configured for independent movement relative to at least one of first or second layers. Foot sleeve 312 further includes an elongated strap 316 extending longitudinally therethrough. Hook element 318 is mounted to elongated strap 316, while hook element 320 is mounted on foot sleeve 312. Foot sleeve 312 further includes a plurality of curvatures 322 for custom fitting about the foot.

With reference to FIG. 7, compression apparatus 400 includes foot sleeve 412 and inflatable member 414 shown in phantom. Foot sleeve 412 includes first and second layers defining a space therebetween that receives inflatable member 414 therein. Inflatable member 414 is configured for independent movement relative to at least one of first or second layers. Foot sleeve 412 includes an elongated strap 416 extending longitudinally therethrough. Hook element 418 is mounted to elongated strap 416, while hook element 420 is mounted on foot sleeve 412. Foot sleeve 412 further includes a plurality of curvatures 422 for custom fitting about the foot. Inflatable member 414 includes inflatable elongated strap portion 424 extending substantially along strap portion 416.

In use, compression apparatus 10, in accordance with the present disclosure, is configured to apply compressive forces to a patient's foot. With reference to FIGS. 8-9, in conjunction with FIGS. 1-4, compression apparatus 10 is positioned about foot F of a patient. Foot sleeve 12 is disposed about foot F by wrapping elongated strap portion 13 around an ankle A, wherein hook element 44 is configured for engaging the surface of outer layer 18. After placement of foot sleeve 12 about foot F and connecting movable inflatable member 14 to pressurized fluid source 38 via inflation assembly 32, controller 40 may then be actuated for supply pressurized air to compression apparatus 10 and initiating compression therapy. Controller 40 intermittently inflates inflatable member 14 sequentially during periodic compression cycles in a pressure gradient profile. As compression therapy is applied, contact layer 16 and inflatable member 14 move independently, while outer layer 18 remains fixed against the foot throughout the compression therapy. The wicking properties of contact layer 16 will facilitate keeping feet F dry during prolonged periods of compression therapy. Deflation between successive inflation cycles occurs by return of air through inflatable member 14 to controller 40, as known in the art. FIGS. 2-7 show various orientations of the several embodiments of the presently disclosed compression apparatus.

Figure 10:
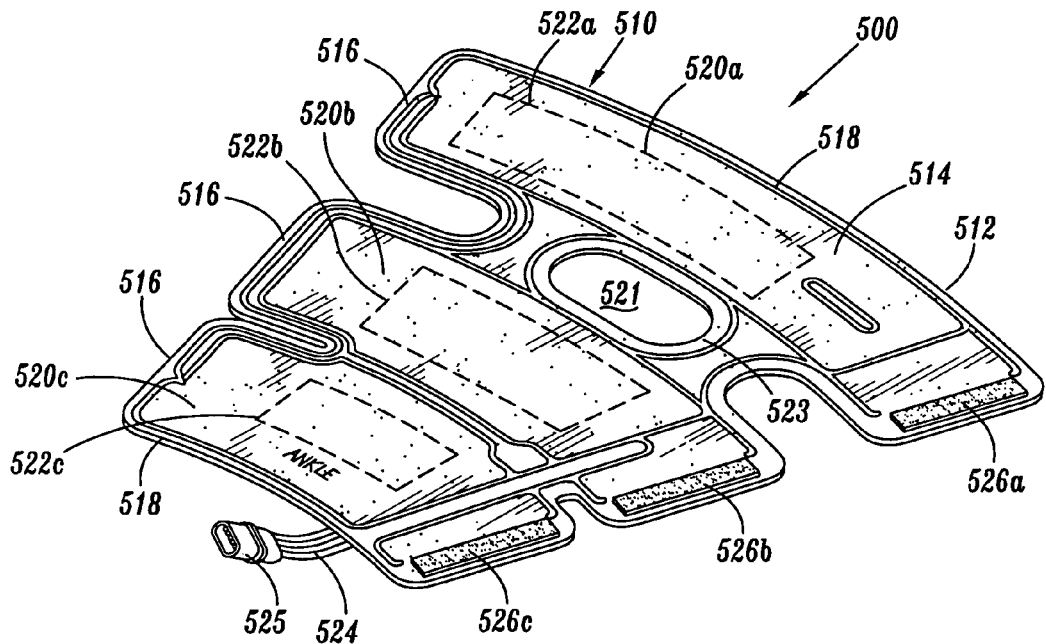
FIG. 10 is a perspective view of another embodiment of the compression apparatus, in accordance with the present disclosure.
Figure 11:
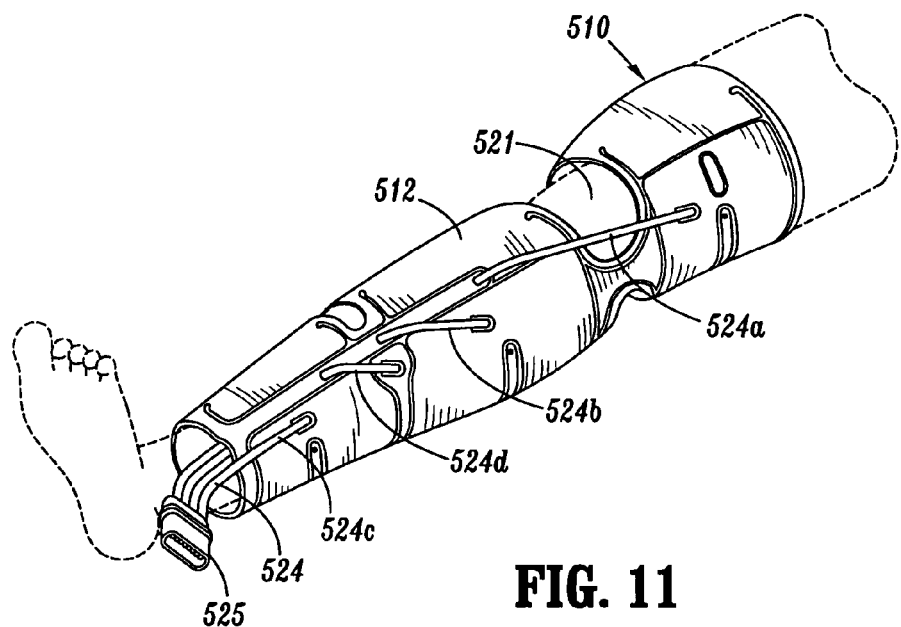
FIG. 11 is a perspective view illustrating the compression apparatus of FIG. 10 wrapped around a leg of a patient.

With reference to FIGS. 10-11, another embodiment of a compression apparatus in accordance with the present disclosure is illustrated and is designated generally as compression apparatus 500. Compression apparatus 500 is adapted for use in a system for applying compressive pressure to a portion of a patient's body, such as, for example, the legs. Compression apparatus 500 is similar to the compression sleeve disclosed in U.S. Pat. No. 5,626,556 to Tobler et al. and U.S. Pat. No. 5,795,312 to Dye that are currently owned by Tyco Healthcare Group LP and are incorporated herein by reference in their entirety.

With particular reference to FIG. 10, the compression apparatus 500, in accordance with the present disclosure, includes sleeve 510 having first or outer sheet 512 and second or inner sheet 514 connected by a plurality of laterally extending sealing lines 516 and longitudinally extending sealing lines 518 connecting the ends of lateral sealing lines 516. Outer sheet 512 is adapted as an outer gas-impervious sheet and second sheet 514 is adapted as an inner gas-impervious sheet, for placement against the person's limbs. Sealing lines 516, 518 may be formed by radio frequency (RF) welding, etc. An elongated opening 521 is provided for extending through what would be the knee region. Opening 521 is defined by peripheral edges 523 extending around opening 521.

Sealing lines 516, 518 define a plurality of spaces or chambers 520a, 520b, and 520c that are adapted for receiving movable inflatable members 522a, 522b and 522c. Inflatable members 522a, 522b, and 522c are configured for moving independently relative to sleeve 510. Similar to inflatable member 14 of compressive sleeve 10, inflatable members 522a, 522b and 522c are adapted for receiving and retaining a pressurized fluid, such as, for example, air, for exerting compressive pressure to the leg of the patient during successive pressure applying cycles. A plurality of lumens 524a, 524b, 524c, and 524d having a valve connector 525 is included for operably connecting inflatable members 522a, 522b and 522c to a controller (not shown) having a source of pressurized fluid, such as, air.

First or outer sheet 512 may, for example, comprise a suitable flexible polymeric material, such as, for example, polyvinyl chloride (PVC) on the order of 5-10 mils thick. Second or inner sheet 514 will preferably comprise a similar polymeric material, e.g. 5-10 mil PVC having laminated to the inner surface to be placed against the limb a non-women material such as polyester for added comfort to the wearer.

Compression apparatus 500 further includes a plurality of hook fasteners for attaching the sleeve about the patient's limb. Hook fasteners include a set of spaced strips, such as loop material, positioned on first or outer sheet 512 and cooperating with a set of spaced hook material 526a, 526b, and 526c disposed on second or inner sheet 514 for releasably fastening compression apparatus 500 encircling the limb.

With particular reference to FIG. 11, in use, after placement of sleeve 510 on the patient's leg and connection to the controller via connector 525 and plurality of lumens 524a, 524b, 524c and 524d, the controller intermittently inflates inflatable members 522a, 522b and 522c sequentially during periodic compression cycles in a pressure gradient profile. As compression therapy is applied, first or outer sheet 512 and inflatable members 522a, 522b and 522c move independently, while second or inner sheet 514 remains fixed against the leg throughout the compression therapy. Deflation between successive inflation cycles occurs by return of air through inflatable members 522a, 522b, and 522c to the controller, as known in the art.

It will be understood that numerous modifications and changes in form and detail may be made to the embodiments of the present disclosure. It is contemplated that numerous other configuration of the compression apparatus and geometries and orientation of the inflatable member may be used, and the material of the sleeve and/or inflatable member may be selected from numerous materials other than those specifically disclosed. Therefore, the above description should not be construed as limiting the disclosed compression apparatus but merely as exemplifications of embodiments thereof. Those skilled in the art will envision numerous modifications within the scope of the present disclosure as defined by the claims appended hereto.

What is claimed is:

1. A compression apparatus comprising:
   a first layer and a second layer defining a space therebetween, the first and second layers each having an outer surface; and
   a single inflatable member having opposite first and second outer surfaces, the inflatable member being disposed in the space and positioned so that the first outer surface of the inflatable member is in direct contact with the inner surface of the first layer and freely movable or repositionable in relation to the first layer, and the second outer surface of the inflatable member is in opposed relation with the inner surface of the second layer;
   an adhesive layer contacting a majority of the second outer surface of the inflatable member and the inner surface of the second layer opposing the adhesive layer to secure the second outer surface of the inflatable member to the inner surface of the second layer, the first layer and inflatable member being free from direct securement to one another, the single inflatable member being free of overlap when disposed on the body part of a patient for providing DVT prophylaxis therapy to a limb of a patient.

2. The compression apparatus of claim 1, wherein the inflatable member has a body portion and a strap portion, the body portion adapted to engage a foot and the strap portion adapted to engage an ankle.

3. The compression apparatus of claim 1, wherein the inflatable member has a body portion that is adapted to engage a foot.

4. The compression apparatus of claim 1, wherein one of the first and second layers includes a foot facing surface that is configured for wicking fluids.

5. The compression apparatus of claim 4, wherein the foot facing surface is maintained in a substantially fixed engagement with a surface of the foot.

6. The compression apparatus of claim 1, wherein the inflatable member includes a lumen for fluidly coupling the inflatable member to a pressure source.

7. The compression apparatus of claim 1, wherein one of the first and second layers is a cushioning layer.

8. The compression apparatus of claim 1, wherein at least a portion of the inflatable member is attached to one of the first layer or the second layers such that the unattached layer is movable in relation to the inflatable member.

9. The compression apparatus of claim 1, wherein the inflatable member is further comprised of one or more inflatable bladders therein.

10. The compression apparatus of claim 2, wherein the strap portion includes a hook with a hook tab for releasably securing the strap portion to an outer surface of the compression apparatus.

11. A compression apparatus of claim 1, wherein the first layer or the second layer is a continuous surface and the layers are sealed along the perimeter to form the space therebetween.

12. A compression apparatus of claim 1, wherein a strap is attached to the inflatable member, and further wherein the strap is inflatable.

13. A compression apparatus of claim 1 wherein the layer of adhesive has a shape which is substantially the same as the shape as the second outer surface of the inflatable member.

* * * * *